US006424921B1

(12) United States Patent
Gupta et al.

(10) Patent No.: US 6,424,921 B1
(45) Date of Patent: Jul. 23, 2002

(54) AVERAGING MULTIPLE HYBRIDIZATION ARRAYS

(75) Inventors: Robert V. Gupta, San Jose; Kirindi V. M. Choi; Robert A. Brahms, both of San Francisco; Doris Chang, Fremont; Darryl V. K. Chong, Mountain View; John D. Burrill; Gregory Marcus, both of Redwood City; Gabor T. Bartha, Mountain View, all of CA (US); Richard Head, Florissant, MO (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/613,167

(22) Filed: Jul. 10, 2000

(51) Int. Cl.[7] ............................ G01N 33/48; C12Q 1/68
(52) U.S. Cl. .............................. 702/19; 435/6; 536/23.1
(58) Field of Search ........................... 435/6; 536/23.1; 702/19

(56) References Cited

U.S. PATENT DOCUMENTS 5,945,522 A * 8/1999 Cohen et al. ............... 536/23.1
6,245,517 B1 * 6/2001 Chen et al. .................... 435/6

FOREIGN PATENT DOCUMENTS

WO    WO 00/71756    * 11/2000

OTHER PUBLICATIONS

Chen et al. (Proc. SPIE–Int. Soc. Opt. Eng. (2000) 3926 (Advances in Nucleic Acid and Protein Analyses, Manipulation and Sequencing) pp. 142–149.*
Dougherty et al. Proc. SPIE–Int. Soc. Opt. Eng. (1997), 3034(Pt. 1, Image Processing, Pt. 1), 68–73.*
Schadt et al. Journal of Cellular Biochemistry (Oct. 20, 2000) vol. 80, pp. 192–202.*
Comander et al. Genome Research (Sep. 2001) vol. 11, pp. 1603–1610.*
Brown et al. PNAS USA (Jul., 2001) vol. 98, No. 16, pp. 8944–8949.*
Strehlow, D. Biotechniques (Jul., 2000) vol. 29, No. 1, pp. 118–121.*

* cited by examiner

Primary Examiner—Mary K. Zeman
(74) Attorney, Agent, or Firm—Fenwick & West LLP

(57) ABSTRACT

Composite hybridization arrays and averaged hybridization arrays are provided. Composite hybridization arrays are formed from a user selected set of hybridization arrays, and once instantiated in a hybridization array database, are available for searching, analysis, and other data processing as with other types of hybridization arrays. This allows otherwise experiments using multiple different nucleotide microarrays to be efficiently consolidated and analyzed. Averaged hybridization arrays provided correctly averaged values from multiple user selected dual channel hybridization arrays.

7 Claims, 7 Drawing Sheets

AVERAGING MULTIPLE HYBRIDIZATION ARRAYS

BACKGROUND

1. Field of Invention

The present invention relates generally to techniques for manipulating hybridizations of gene expression microarrays.

2. Background of the Invention

Hybridization is a powerful and versatile technique for sequencing, detecting and localizing nucleic acids. In the general area of molecular biology, hybridization is used to map genes, detect gene expression and over-expression, diagnose diseases, identify pre-disposition to diseases, and the like.

In general, labeled nucleic acid probes are hybridized to target samples and hybridization then detected. The target samples can be in solution or they can be immobilized on a solid surface, such as in arrays and microarrays. More specifically, a gene expression microarray generally comprises a number of gene sequences distributed in an array on a substrate. Each array element is a DNA sequence, and allows the measurement of the expression of a gene in one or more samples. A typical method of using microarrays involves contacting nucleotide sequences contained in a fluid with the sequences immobilized on the microarray under hybridization conditions, and then detecting the hybridization complex. The resulting hybridrized microarray is commonly referred as a hybridization, or simply a 'hyb.' The resultant pattern of hybridized nucleic acids provides information regarding the genetic profile of the test array.

A widely used method for detecting the hybridization complex in microarrays is by fluorescence. In one method, probes derived from a biological sample are amplified in the presence of nucleotides that have been coupled to a fluorescent label (reporter) molecule so as to create labeled probes. The labeled probes are then incubated with the microarray so that the probe sequences hybridize to the complementary sequences immobilized on the microarray. A laser scanner is then used to determine the levels and patterns of fluorescence.

The use of fluorescence detection in microarray analysis is disclosed in U.S. Pat. No. 5,888,742 to Lal et al. for the detection of altered expression of human phospholipid binding protein (PLBP) and in U.S. Pat. No. 5,891,674 to Hillman et al. for the monitoring of the expression level of insulin receptor tyrosine kinase substrate (IRS-p53h), and to identify its genetic variants, mutations and polymorphisms for determining gene function, and in developing and monitoring the activity of therapeutic agents.

The above described hybridization detection method is known as single channel hybridization. This approach provides generally a single measure of the hybridization for each sequences, but does not provide any differential information about relative amounts of hybridization between different samples. To obtain relative hybridization rates, a more complex process known as competitive hybridization is used. In this process, two samples of nucleotides from a particular tissue or other specimen are bound to fluorescent label, each lable having distinctive emission/absorption spectra. Typically one sample has a fluorescent dye of one color (e.g. green), the other sample having a different color dye (e.g., red). Typically one of the samples is a control sample, and the other the experimental sample. The labeled samples are contacted with the microarray under hybridization conditions so the labeled sequences bind with various ones of the sequences on the array. A laser scanner is then used to measure the degree to which the two differently labeled samples have hybridized the microarray. More particularly, a measure of the transcript abundance values for each of the red and green samples is obtained for each array element. The ratio of the red and green transcript abundance values is call the fold difference, and it provides a measure of the relative abundance of the MRNA in the two hybs, with respect to each array element (gene sequence). This can inform the researcher, for example, of the change in MRNA abundance in the experimental sample relative to the control.

The number of gene sequences (array elements) that can be analyzed in this way is limited by the size of the substrate and manufacturability limitations, but is typically less than all of the gene sequences of interest to a researcher. For example, one commercially available type of microarray from Incyte Pharmaceuticals, Inc. contains 10,000 gene sequences. However, over 100,000 gene sequences have been identified. Currently, a researcher wanting to analyze a particular sample against the entire database of gene sequences must perform at least 6 different hybridizations, one on each microarray of 10,000 sequences. Each of the resulting hybs must be separately analyzed and searched during subsequent research. The handling of multiple separate hybs is cumbersome and inefficient. Thus, it is desirable to provide a way for the researcher to combine hybs from different microarrays in a manner that allows them to be queried and otherwise processed as a single hyb.

In performing genetic analysis, it also desirable to obtain a sense of the variability of the hybs derived from the same sample. More specifically in some instances it is desirable to be able to average the relative transcript abundance values from two or more hybs. However, because the relative transcript abundance values that describe the hybs are ratios, conventional arithmetic averaging gives incorrect averaged values. Accordingly, it is desirable to provide a way to correctly average the relative abundance values from multiple hybs.

SUMMARY OF THE INVENTION

The present invention overcomes the limitations of conventional hyb manipulation tools and techniques by providing for the creation and manipulation of composite hybs and averaged hybs. A composite hyb is formed from a user selected number of different hybs that have a same technology type, and a same technology specific data source. The composite hyb can be treated as a single large hyb over the entirety of the multiple arrays. The researcher can interact with a composite in the same manner as regular hybs, including searching, visualization, or other types of data processing. A given individual hyb may be made a part of any number of different composite hybs. Beneficially, the underlying data from the selected hybs is preserved and always available to the researcher. In one embodiment, to avoid explosive proliferation of the hyb data, particularly where a hyb is a member of many composite hybs, the hyb data is not replicated in each composite hyb. Istead, each composite hyb utilizes the original data of its underlying hybs. Alternatively, where data storage limitations are not as significant, duplication of the underlying data may be implemented. A composite hyb may be created from other composite hybs or from averaged hybs.

The present invention also provides for the construction of averaged hybs. A number of hybs of a given sample are selected by the user, and a correct determination of the average relative transcript abundance value for each array element is computed and stored. The researcher can then treat the averaged hyb in the same manner as an individual hyb, and obtain the additional benefit of the robustness of the averaged values. A further beneficial feature is the ability to form a composite hyb from multiple averaged hybs.

The features and advantages described in this summary and the following detailed description are not all-inclusive, and particularly, many additional features and advantages will be apparent to one of ordinary skill in the art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

The figures depict a preferred embodiment of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF THE PREFERRED EMBODIMENT

Overview

Figure 1:
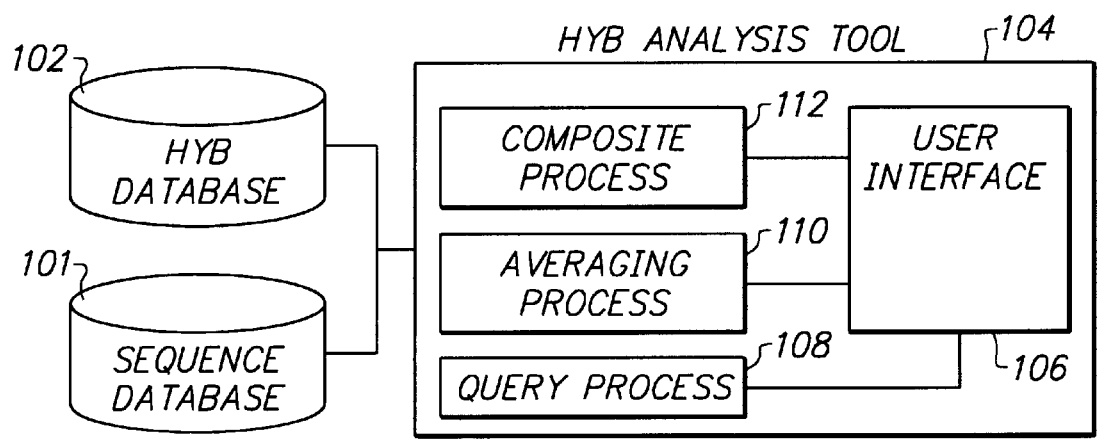
FIG. 1 is a high-level block diagram illustrating a system for providing composite and averaged hybs.

Referring now to FIG. 1, there is shown an illustration of one embodiment of a system for practicing the present invention. In this typical embodiment, the system 100 includes a sequence database 101, a hybridization ('hyb') database 102, and a hybridization analysis tool 104. These elements are communicated with each other over a network, for example a LAN, WAN, or the Internet.

Figure 4:
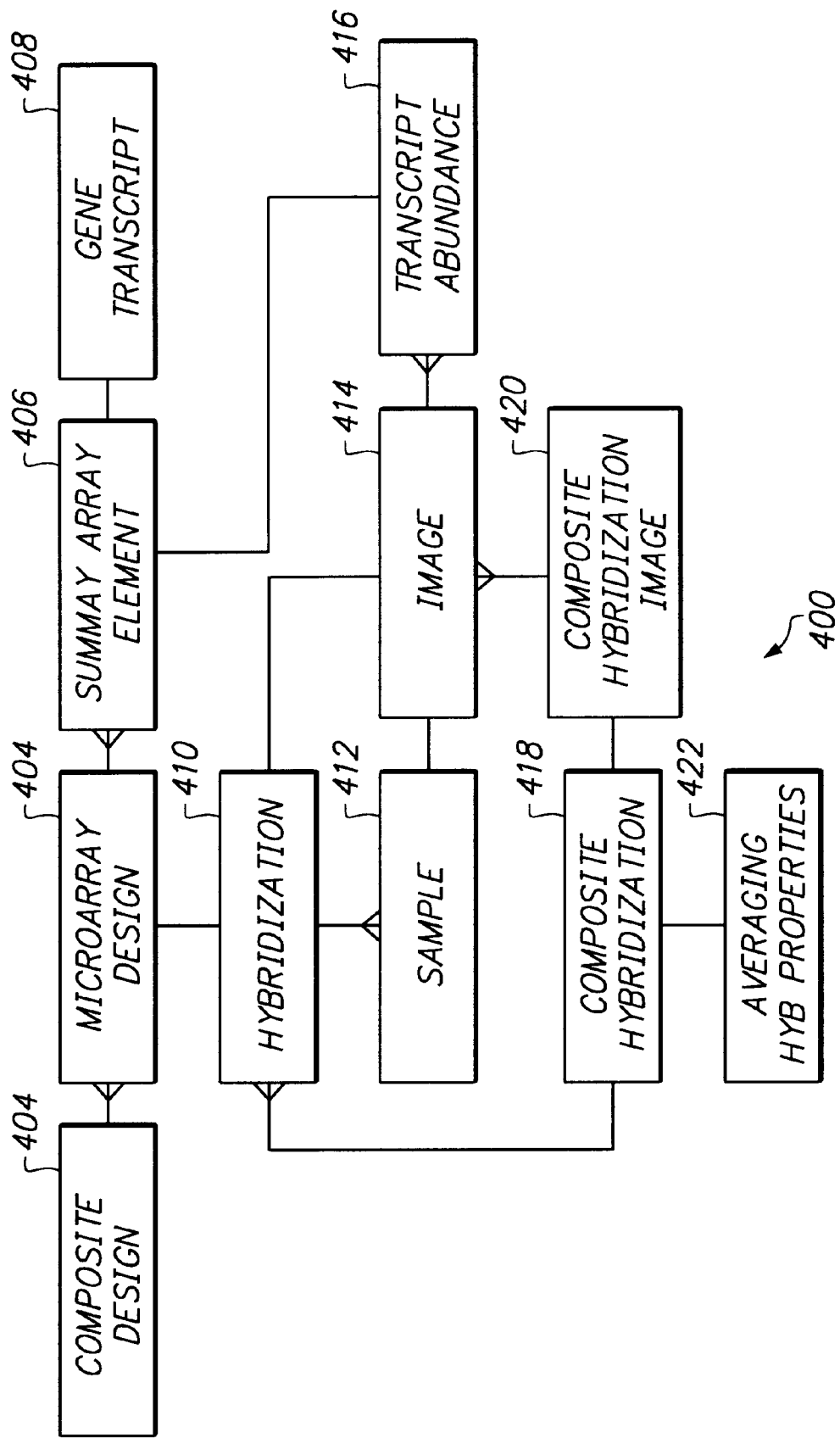
FIG. 4 is a database schema of the database providing composite and averaged hybs.

The sequence database 101 may be any public available gene sequence database (e.g., various GenBank database) or any privately developed database (e.g. sequence databases from Incyte Pharmaceutical). While a single sequence database is shown, multiple such databases may be used concurrently. The hyb database 102 contains hybs that have been created from the application of prepared samples to selected gene microarrays. The mechanisms by which the hybs are created are not material to the details of this invention. A portion of a data model of the hyb database 102 relevant to composite and averaged hybridizations is illustrated in FIG. 4, and will be discussed in more detail, below.

The hyb analysis tool 104 is a software product that is stored in a computer readable medium (e.g. computer RAM) and executes on a conventional computer process (e.g., an Intel Pentium®), and preferably runs as a plug-in with conventional browsers (e.g., Microsoft Corp. Internet Explores®, or Netscape Communications, Inc. Navigators®). This allows the tool to access the databases 102, 101 via existing web protocols (e.g., TCP/IP and HTTP). The development of software products and databases is conformance with web protocols and standards is well understood by those of skill in the art, and not further discussed here. In one embodiment, as illustrated, the hyb analysis tool 104 includes a hyb composite process 112, a hyb averaging process 110, one or more query processes 108, and a user interface 106 for accessing and controlling the various processes. One exemplary embodiment of the hyb analysis tool 104 is LifeArray 2.0®, available from Incyte Pharmaceutical, Inc. of Palo Alto, Calif.

The user interface 106 includes various screen displays including fields and user selectable controls, which allow a user to select various of the processes for execution, and further select sequences and hybs from their respective databases for manipulation. Generally, the user interface enables the user to define and execute queries for searching the sequence database 101 using the query processes 108, to view search results and hybs using various types of graphical and tabular viewers, and to define and describe the properties and attributes of hybs, including forming composite and averaged hybs. Various screen displays of the user interface are illustrated below with respect to FIGS. 5 and 7.

Figure 2:
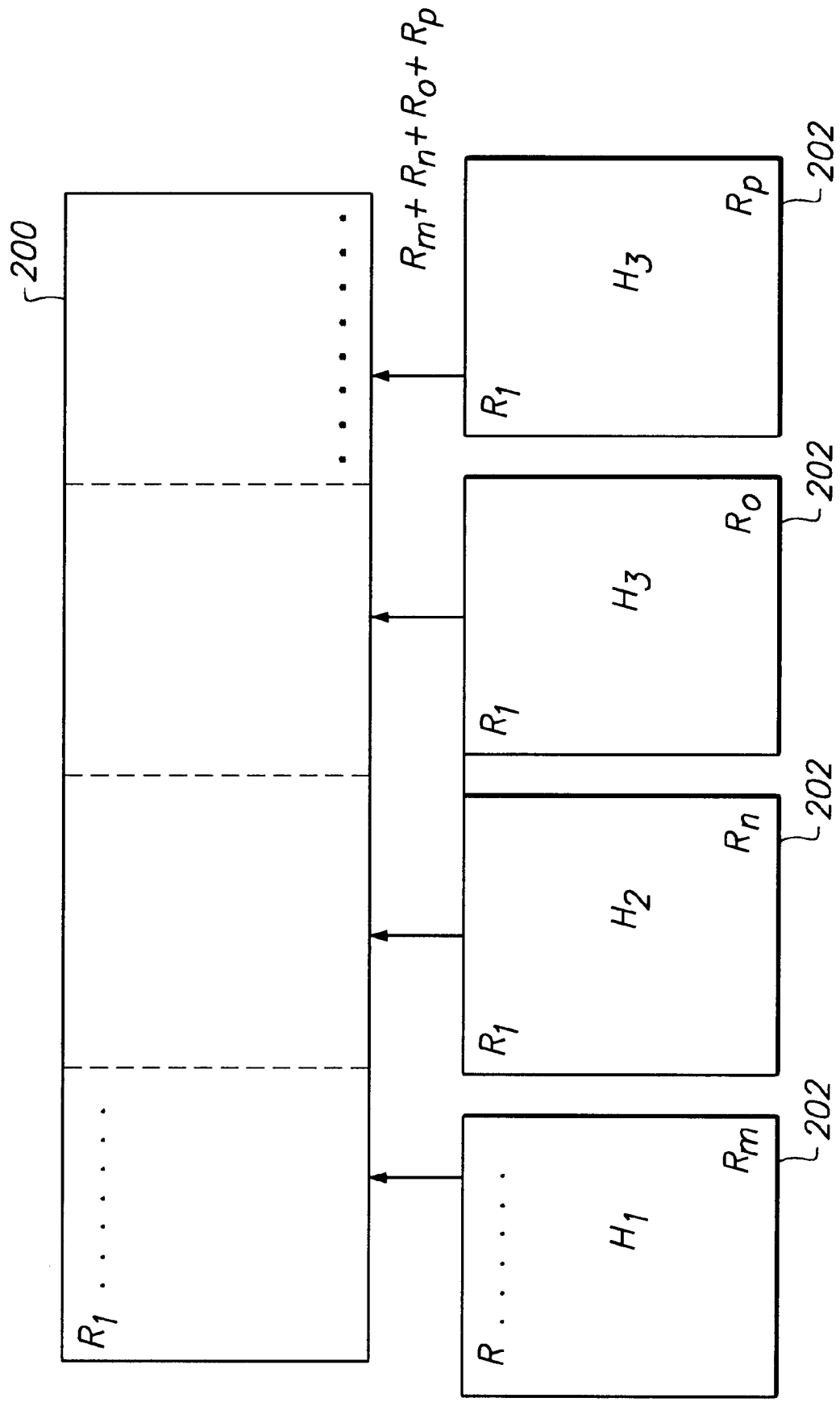
FIG. 2 is a conceptual diagram illustrating the formation of a composite hyb.

Referring now to FIG. 2 there is shown a conceptual diagram of the formation of a composite hyb from multiple hybs. A composite hyb 200 may be understood as the concatenation of a user selected set of constituent hybs 202. For purpose of illustration this composite hyb 200 is formed from four constituent hybs 202, H1 to H4, through obviously a composite hyb 200 may formed from as few as two constituent hybs to as many as desired or practical for the application or underlying database system. Each of the constituent hybs 202 has a number of array element R. Constituent hyb H1 has Rm elements hyb H2 has Rn elements, hyb H3 has Ro elements, a hyb H4 has Rp elements. In some instances the number of elements in each constituent hyb is the same, e.g. 10,000 array elements. However, the present invention allows hybs having different array designs to be composited. Once composited, the resulting composite hyb 200 has an effective or virtual array design with the total number of the elements from its constituent hybs. Thus, the illustrated composite hyb 200 has a total of Rm+Rn+Ro+Rp elements. Once formed, the composite hyb 200 is stored in the hyb database 102.

In a preferred embodiment, all constituent hybs 202 have a same technology type and a same data source, but as noted may have different array designs. In addition, the constituent hybs may come from different samples that were prepared under different conditions.

Figure 3:
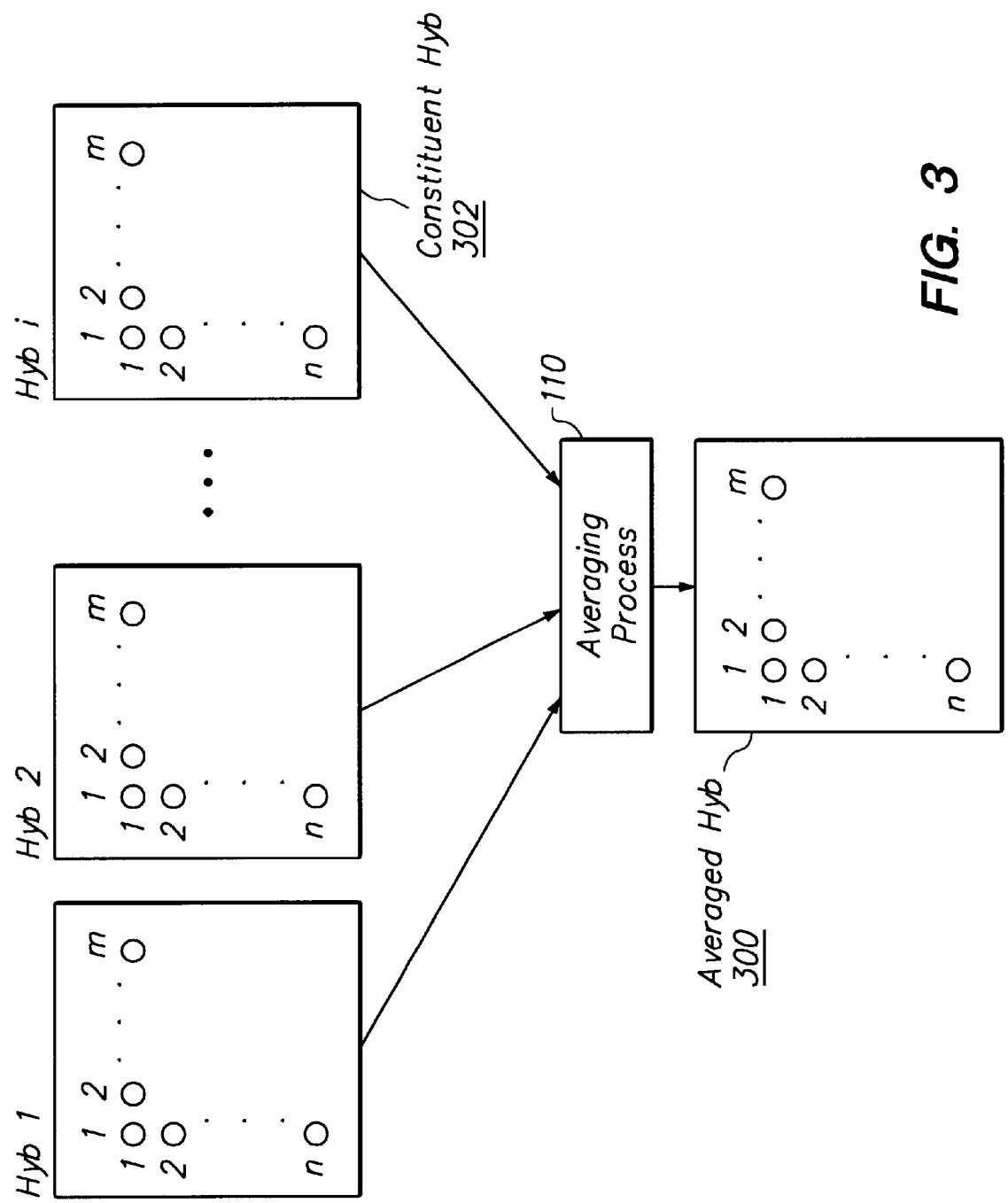
FIG. 3 is a conceptual diagram illustrating the formation of an averaged hyb.

Referring now to FIG. 3 there is shown a conceptual diagram of the formation of averaged hybs. The averaged hyb 300 is formed from a user selected number of constituent hybs 302, here hybs $H_1$ to $H_i$. Here, each hyb $H_i$ has the same array design, sample, and normalization method and summarization method. Each constituent hyb 302 has m columns and n rows, forming m×n array elements. Each array element is a relative transcript abundance value, which is the ratio of two transcript abundance measures, one from each of two samples for the hyb, such as a control and experimental sample. This makes each of the hybs 'replicates' of each other with respect to their structural features. Obviously the actual underlying relative abundance values of the array elements will vary, and the averaged hyb 300 enables the manipulation of a correct average relative abundance value. More particularly, the hyb averaging process 110 takes as inputs the array elements $R_{m,n}$ from $H_i$ constituent hybs, computes a correct average relative abundance value for each array element $R_{m,n}$. The complete averaged hyb 300 is then stored in the hyb database 102. Accordingly, each hyb $H_i$ must have the same array design in order to be averaged.

Data Model

Referring now to FIG. 4 there is shown one embodiment of a schema for the hyb database 102 that has the beneficial feature of supporting both composite hybs and averaged hybs. In this schema 400, a hybridization 410 is comprises a microarray design 404, and one more samples 412. The hybridization 410 includes attributes such as name, date, experiment name and ID, technology type, data source, modification dates, hyb ID, and so forth as may be useful to catalog each hyb.

The microarray design 404 includes attributes defining the array design, such as matrix dimensions (number of horizontal and vertical elements) and purpose or use. The microarray design 404 includes a number of summary elements 406, each of which has a fixed location in the design 404 (e.g. a row/column position). Each of the array elements 406 is also associated with a particular gene transcript or sequence 408. Each of the array elements 406 is further associated a relative transcript abundance value 416 for the gene transcript at the given location.

Each sample 412 is further associated with an image 414, which is either a scanned image or a signal averaged image; each image has an ID and a filename. Each image 414 is also associated with a number of transcript abundance values 416. When an averaged hyb is created, the average relative transcript abundance values are stored by the transcript abundance 416 data structure.

A composite hyb 408 data structure provides for database persistence of both composite hybs and averaged hybs. This feature makes it unnecessary to separately define an averaged hyb data structure, and thereby provides increased database efficiency. The composite hyb 408 includes attributes such as name (which will be different from the names of its constituents), creation date, and private/public tag; other attributes are inherited from the constituent hybs. The private/public tag lets a user determine whether a composite hyb is available to all others (public) or available only to the user (private). If user groups are supported in the database (not shown) the user may define which user groups have access to the composite hyb.

The composite hyb 408 is a composite of a number of hybs 410 as illustrated. Each composite hyb 418 further has an association with a composite microarray design 402, which itself is composited of a number of microarray designs 404. If an existing composite design 402 exists at the time a new composite hyb 418 is created, it is reused. In one embodiment, when a new composite design 402 is created, the summary array elements 406 for each of the constituent microarray designs 404 are copied into the database 110 with a new microarray design ID. In an alternative embodiment, a new composite design 402 is created, but contains references to the underlying constituent array data, rather than duplicating it. The composite hyb 408 further has an association with a composite hyb image 420, which itself it composited over multiple images 414.

To support averaged hybs, the composite hyb 408 has an association with an averaged hyb properties structure 422. This structure defines the properties used to construct the averaged hyb, such as averaging method. The averaging process 110 uses the attributes of the averaged hyb properties structure 422 to determine the appropriate averaging methodology.

As can be seen from the data model, a composite hyb may be created from other composite hybs or from averaged hybs.

Composite Hybs

Figure 5:
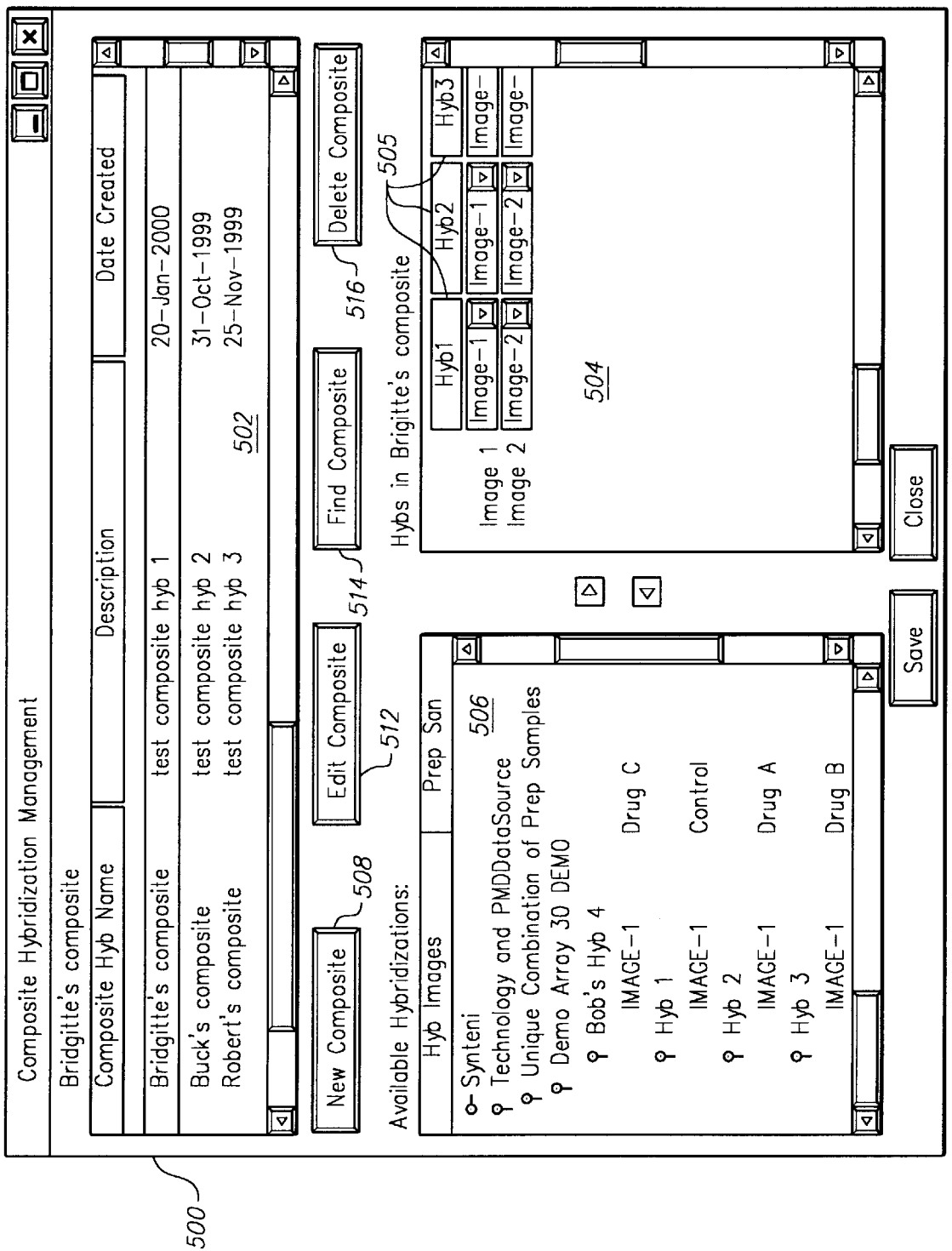
FIG. 5 is a screen display of a software tool providing support for creating and manipulating composite hybs.

Referring now to FIG. 5, there is shown a user interface of the hyb analysis tool 104 for manipulating composite hybs. This composite hybridization management window 500 allows a researcher to view and create composite hybs. The upper panel 502 displays a list of existing composite hybs, including their name or description, and their creation date. When the window is opened, no composite hybs are selected, but the available ones are displayed.

The bottom right constituent hybs panel 504 lists the constituent hybs 505 that make up a composite hyb currently selected in the upper panel 500. The constituent hybs 505 are listed horizontally (here scrolled out of view) and by their images. If no composite hyb is selected in the upper panel 502, then the constituent hyb panel 504 is empty.

The available hybs panel 506 on the lower left shows the hybs that are available in the database for use in a composite hyb. If the user enters the window 500 from the query processes 108, where a number of hybs have been identified from a query (hyb working set), then this panel 506 is populated with the hyb working set. The available hybs panel 506 lists these hybs hierarchically, first by technology type and data source, and then by unique combination of samples. Various buttons are provided to facilitate management of composite hybs. A researcher can create a new composite hyb with the new composite button 508, which instantiates a new database record for the composite. The user is prompted for a new name of the composite hyb, which is preferably suggested automatically by the database 102 to include an indication that the new hyb is a composite (e.g. "new composite hyb"). When specifying the name of a new composite hyb the user also specifies a name of an experiment to which the composite pertains.

Once the empty, new composite hyb is created, the user can then add (or remove) hybs from the available hybs panel 506. A newly created composite hyb is listed in the composite hyb panel 502, and selected automatically to enable its editing. Arrows 510 are used to selectively add or remove a hyb. The added hybs show up in the right panel 504. Once the user has finished adding constituent hybs, he clicks the save button 514. This updates the hyb database 112, and commits any changes made the composite hyb.

The user can edit the name and description of a selected composite hyb using the edit button 512. The user can find a composite hyb using the find composite button 514 to execute the appropriate database (e.g. SQL) search; the search of the database maybe performed on any of the attributes of the composite hyb in the same manner that other hybs are retrieved.

The user may delete a currently selected composite hyb from the composite hyb panel 502 using the delete composite button 516. The database administrator may establish access privileges that control which users have the ability to create, edit, or delete composite hybs.

The query process 110 supports various types of querying of hybs, such as BLASTA, BLAST2, FASTA, and so forth.

To facilitate the present invention, the user can delimit these queries to include both regular and composite hybs, or either type individually. Likewise, search results of hybs satisfying a query are preferably displayed along with an indication of whether they are regular or composite hybs.

Figure 6:
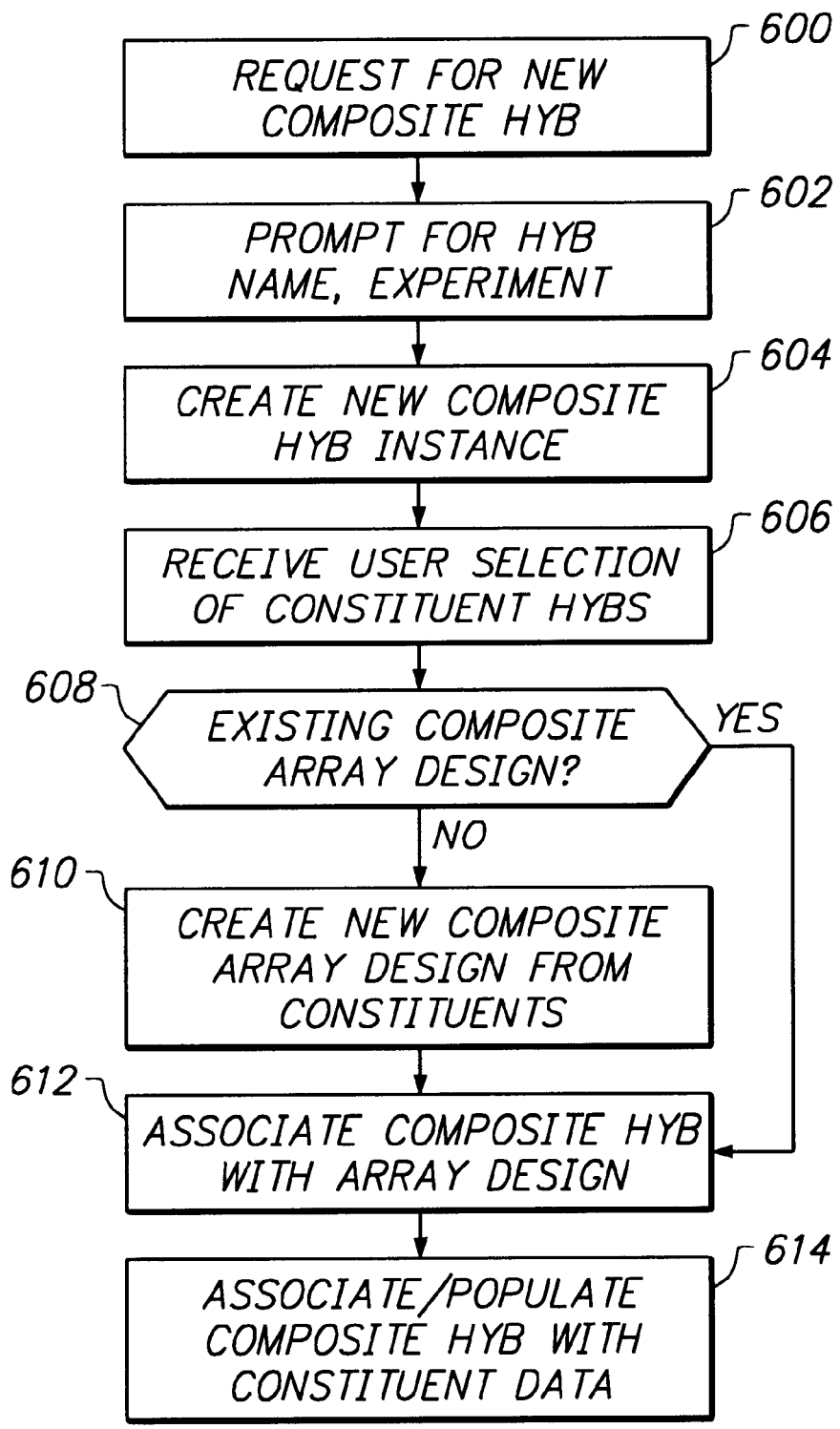
FIG. 6 is a flowchart of a process for forming a composite hyb.

FIG. 6 illustrates a flowchart of a process for creating a composite hyb in the hyb database 102, as managed by a composite hyb process 112 executed by the hyb analysis tool 104. First, the process 112 receives 600 a request to create a new composite hyb. This will come from the user, for example by clicking the new composite button 508. The user is prompted 602 for a name and experiment description of the new composite hyb. Upon entry by the user, the process 112 creates 604 a new instance of a composite hyb 418 in the database, and displays the named composite hyb in the composite hyb panel 502, as noted above. The process 112 then receives 606 from the user a number of selections of available hybs to be the constituent hybs. Once the user is done, and saves the composite hyb the hyb database 102 is updated, as follows.

First, the process 112 determines 608 if there is an existing composite array design 402 for this new composite hyb 418. If so, the process 112 associates 612 the new composite with this array design 402. Otherwise, the process creates 610 a new composite array design 402 from the array designs 404 of the selected constituents, and associates 612 it with the new composite hyb 418.

In one embodiment, for each of these constituent hybs, the process 112 creates 614 the appropriate associations between the new composite hyb and its constituents. In an alternative embodiment, for each of these constituents, the process 112 duplicates 614 the constituent hyb's data, particularly, its image 414, its transcript abundance 416, and its sample 418. In either case, the result is that access to the composite hyb provides access to all of the underlying constituent data.

Averaged Hybs

Figure 7:
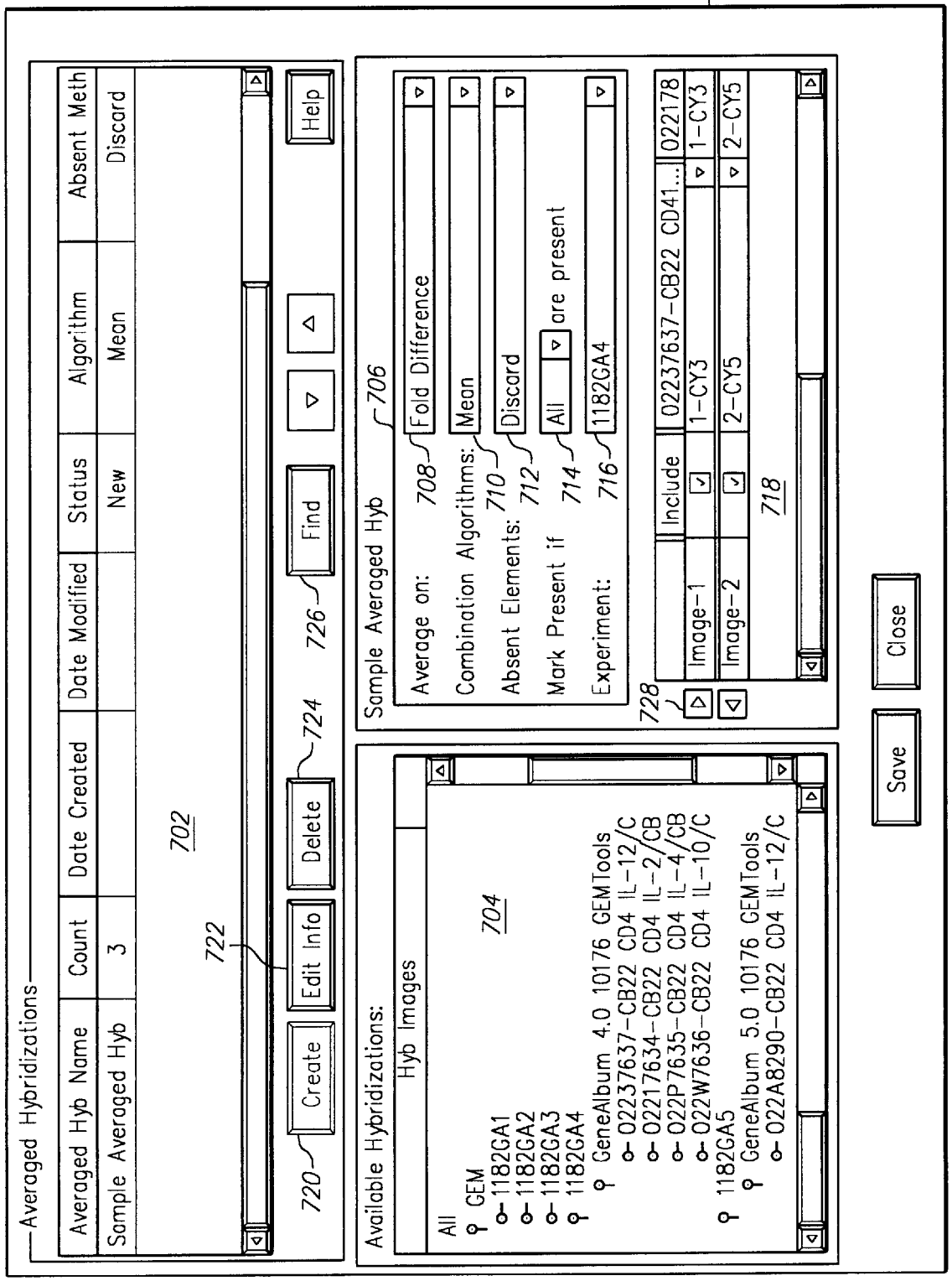
FIG. 7 is a screen display of a software tool providing support for creating and manipulating averaged hybs.

Referring now to FIG. 7 there is shown a user interface of the hyb analysis tool 104 for creating and managing averaged hybs. In this window 700, the user can create, edit, delete and find averaged hybs in the hyb database 102. In the averaged hyb management panel 702, there are listed averaged hybs that have been previously created. In this panel, each averaged hyb is shown with its name, count (number of hybridizations used to create the averaged values), date created, date modified, averaging status, averaging algorithm used, method for handling absent values, and present method (e.g. present, absent, or marginal). Create button 720 allows the user to create a new averaged hybridization; edit button 722 enables editing of name, experiment, and other information for an averaged hybridization selected in panel 702. Likewise, the user can delete a selected averaged hybridization with button 724.

The available hybridization panel 704 lists hybs that have been returned from the current query by the query processes 110. If the averaged hybridization window 700 is opened before a query is executed, then this panel 704 is empty. If the panel 704 is opened after a query is executed, then it is populated, as shown for example, with hybs having the same summarization and normalization methods.

The averaged hyb creation panel 706 lists the details of an averaged hyb selected in panel 702, and is used to define the attributes of an averaged hyb. To create an averaged hyb, the user first executes a query on the hyb database 102 to obtain a working set of hybs. In the averaged hyb window 700, the user selects the create button 720, and enters a name for the averaged hyb. The available hybs returned from the query are listed in the available hybs panel 704; from here the user selects two or more regular (non-composite) hybs, which are added to the hyb creation panel 706 via the add button 728.

The user selects the appropriate parameters for defining the averages, including the selection 708 of averaging on relative transcript abundance (here called 'fold difference'). The combination algorithm 710 for averaging on relative transcript abundance is shown here as a mean type average, the process of which is further explained below. The user can also specify how absent elements 712 in the array are handled, whether they are discarded, included, or replaced by a value equal to the lowest value of present elements during the averaging. The user can further specify how elements which are present in all hybs being averaged are marked, including marking only if all hybs have the element, marking if a majority of the hybs have the element, and marking if any of the hybs have the element. Experiment field 716 lists the experiment from which the constituents of the averaged hyb are drawn.

As noted above, each hyb array has a number of elements $R_{m,n}$, each of which stores a quotient F of two transcript abundance values:

$$F = \frac{T1}{T2};$$

where T1 is the transcript abundance value for one channel/sample (e.g. Cy3) and T2 is the transcript abundance value for another channel/sample (e.g., Cy5). F here is called the fold difference, and as noted there are numerous F values for a given array, such as 10,000 for an GEM® microarray. Notice that because fold differences are ratios of positive values, they are always have a positive sign. An increase in transcript abundance between two samples (up-regulation) is indicated by F>1.00, while a decrease (down-regulation) is indicated by F<1.00.

Figure 8:
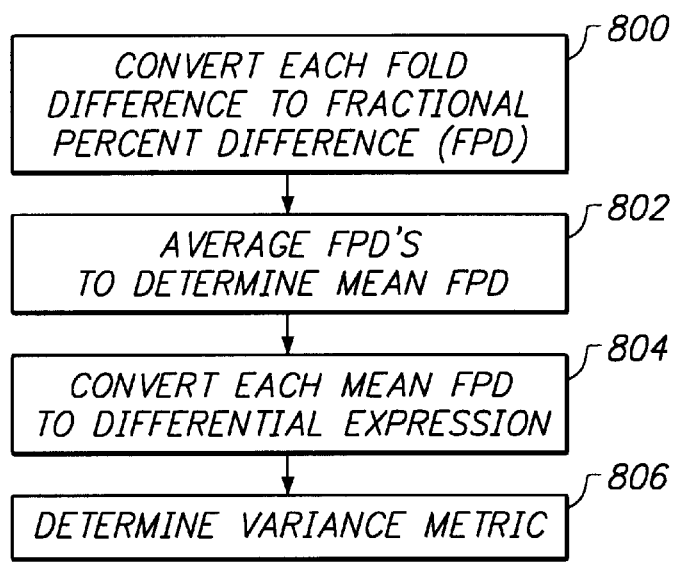
FIG. 8 is a flowchart illustrating a process for forming averaged hybs.

FIG. 8 illustrates a flowchart of one embodiment of a process for averaging hybs, as may be implemented by the averaging process 110. For ease of explanation, the averaging process 110 is described with respect to a given array location $R_{m,n}$ storing a fold difference $F_i$, where i indexes over multiple hyb arrays N, i=1 . . . N.

In accordance with the present invention then, the averaging methodology converts each fold difference $F_j$ to a differential expression (DE) value in a positive/negative scale. This positive/negative scaling expresses up-regulation as DE>0, while down-regulation is indicated by DE<0. The DE value for values of F is calculated as follows:

If ≧1, then the DE value is F;

If<1, then the DE value is $$\frac{-1}{F}.$$

This provides a domain of DE values: [−∞, −1)∪[1, ∞).

Next, each of the DE values is converted to a fractional percent difference (FPD), which has values between —1 and 1.

If DE≧1, then FPD=DE−1;

If DE≦−1, then FPD=DE+1.

This explanation has drawn out the individual steps of the DE and FPD computation for clarity. In practice—for example in one implementation of the averaging process 110 and as illustrated in FIG. 8—the determination of the FPD value for F can be computed 800 in a single step directly from the values of F (or from T1 and T2):

If $F \geq 1$, then FPD=F−1;
Else FPD=−F+1.

The average of the FPD's is then calculated 802 for the corresponding array locations $R_{m,n}$, across the multiple hybs:

$$\overline{FDP} = \frac{1}{N}\sum_{i=1}^{N} FPD_i$$

The resulting mean $\overline{FDP}$ is then converted 804 back to a DE value:

If $\overline{FDP} \geq 0$, then DE=$\overline{FDP}$+1;
If $\overline{FDP} < 0$, then DE−$\overline{FDP}$−1.

The resulting differential value DE is the mean value in a positive/negative scale, over the range:

$$[-\infty, -1) \cup [1, \infty)$$

which can then be converted, if desired to a normal scale, that is from DE values to FDP, and then to T1 and T2.

The averaging process 110 repeats this set of calculations for each array location $R_{m,n}$, e.g. for each of the 10,000 array locations in a given microarray. It should be noted that the averaging process 110 may calculate the various values either across each of the hybs first, before proceeding with the next array element (as described), or it may compute the FPD values for all elements in each array first, and then calculate the averages, and final DE values. These and other algorithmic implementations are equivalent.

Once the mean FPDs are calculated, an optional calculation 806 by the averaging process 110 is the variation metric. Here, the averaging process 110 calculates the standard deviation SD for each array element $R_{m,n}$:

$$SD = \sqrt{\frac{1}{N}\sum_{i=1}^{N}(FPD_i - \overline{FPD})^2}$$

The floored mean for each of FPD values, $\overline{FPD}_f$, is then computed:

If $|\overline{FPD}| > 1$ then $\overline{FPD}_f = |\overline{FPD}|$;
Else $\overline{FPD}_f = 1$.

The variation metric CV is then calculated as:

$$\% CV = \frac{100\ SD}{\overline{FPD}_f}.$$

In summary, the present invention provides two useful new forms of hybridization arrays. Composite hybridization arrays allow for the consolidation of hybridizations from multiple constituent arrays into a single array that can be searched and analyzed as if it were created from a single experiment. This allows the researcher to more efficient review and organize the hybridization results from different experiments with respect to a greater number of sequences. Averaged hybridization arrays assist the researcher in analyzing the variability of relative transcript abundance values over multiple hybridization arrays. As will be understood by those familiar with the art, the invention may be embodied in other specific forms without departing from the spirit or essential characteristics thereof. For example, the averaging process and the composite process may be separated into different executable software products, for example different browser plugins, instead of in a single plugin. Also, different algorithm implementations of the averaging process may devised which are equivalent to the described implementations in that they yield the same quantitative results. Accordingly, the disclosure of the present invention is intended to be illustrative, but not limiting, of the scope of the invention, which is set forth in the following claims.

we claim:

1. A computer-implemented method of averaging a plurality of hybridization data arrays, each hybridization data array having a plurality of array locations storing relative transcript abundance ratios, each relative transcript abundance ratio being the ratio of two hybridization measures and having a positive value greater than 0.0, to provide a single averaged hybridization data array having an averaged relative abundance value in each of the array locations, the method comprising:

for each array location on each of the plurality of arrays, converting the relative transcript abundance ratio to a fractional percent difference value (FPD) having a value over a range of at least −1 to 1, to provide a plurality of FPD's;

for each array location, determining an average FPD from the plurality of FPD's;

for each array location, converting the average FPD to a differential expression (DE) having a value in the range $[-\infty, -1) \cup [1, \infty)$, the DE values representing the averaged relative transcript abundance ratios; and storing the plurality of DE values in an averaged hybridization data array.

2. The computer implemented method of claim 1, wherein converting the relative transcript abundance ratio to a fractional percent difference value (FPD) further comprises:

converting the relative transcript abundance ratio to a DE having a value in a range from $[-\infty, -1) \cup [1, \infty)$; and converting each DE to an FPD having a value in the range of at least $[-1, 1)$.

3. The computer implemented method of claim 2, wherein converting each DE to an FPD having a value in the range of at least $[-1, 1)$ further comprises:

converting each DE to an FPD according to the equations:
if $DE \geq 1$, then FPD=DE−1; and
if $DE \leq -1$, then FPD=DE+1.

4. The computer implemented method of claim 1, wherein converting the relative transcript abundance ratio to a fractional percent difference value (FPD) further comprises:

if $F \geq 1$, then FPD=F−1; and
if $F < 1$, then FPD=−F+1,
where F is the relative transcript abundance ratio.

5. The method of claim 1, further comprising:
computing for each averaged relative transcript abundance ratio a variation metric.

6. The method of claim 5, wherein computing for each averaged relative transcript abundance ratio a variation metric comprises:

computing a standard deviation SD for the averaged relative transcript abundance ratio;

computing a floored averaged relative transcript abundance ratio $\overline{FPD}_f$;

computing the variation metric CV as:

$$CV = \frac{100\ SD}{\overline{FPD}_f}.$$

7. A computer program product, stored on a computer readable medium, and including computer executable instructions for controlling a processor to create an averaged hybridization data array from a plurality of hybridization data arrays, each hybridization data array having a plurality of array locations storing relative transcript abundance ratios, each relative transcript abundance ratio being the ratio of two hybridization measures and having a positive value greater than 0.0, to provide a single averaged hybridization data array having an averaged relative abundance value in each of the array locations, the computer program product causing the processor to perform a method comprising:

for each array location on each of the plurality of arrays, converting the relative transcript abundance ratio to a fractional percent difference value (FPD) having a value over a range of at least [−1, 1) to provide a plurality of FPD's;

for each array location, determining an average FPD from the plurality of FPD's;

for each array location, converting the average FPD to a differential expression (DE) having a value in the range [∞, −1)∪[1, ∞), the DE values representing the averaged relative transcript abundance ratios; and storing the plurality of DE values in an averaged hybridization data array.

\* \* \* \* \*

UNITED STATES PATENT AND TRADEMARK OFFICE
CERTIFICATE OF CORRECTION

PATENT NO. : 6,424,921 B1
DATED : July 23, 2002
INVENTOR(S) : Gupta et al.

It is certified that error appears in the above-identified patent and that said Letters Patent is hereby corrected as shown below:

<u>Title page,</u>
Item [75], Inventors, please replace "Robert V. Gupta" with -- Robert P. Gupta --; and please replace "Kirindi V.M. Choi" with -- Kirindi V. M. Choi, Jr. --

Signed and Sealed this

Twenty-third Day of September, 2003

JAMES E. ROGAN
*Director of the United States Patent and Trademark Office*